United States Patent [19]

Hirayama et al.

[11] Patent Number: 4,948,816
[45] Date of Patent: Aug. 14, 1990

[54] SPHERICAL GRAINS OF POLYAMINO ACID AND PRODUCTION METHOD THEREOF

[75] Inventors: Chuichi Hirayama, No. 373-12, Shimonabe-machi, Kumamoto-shi, Kumamoto-ken; Yoshiaki Motozato, No. 1174-5, Hotakubohonmachi, Kumamoto-shi, Kumamoto-ken; Hirotaka Ihara, No. 854-2, Shimizu-machi, Takahira, Kumamoto-shi, Kumamoto-ken, all of Japan

[73] Assignees: Chuichi Hirayama; Yoshiaki Motozato; Hirotaka Ihara; Juridical Foundation the Chemo-Sero-Therapeutic Research Institute; Mitsui Toatus Chemical, Inc., all of Japan

[21] Appl. No.: 368,558

[22] Filed: Jun. 20, 1989

Related U.S. Application Data

[60] Division of Ser. No. 117,925, Nov. 3, 1987, which is a continuation-in-part of Ser. No. 878,683, Jun. 26, 1986, abandoned.

[30] Foreign Application Priority Data

Jun. 27, 1985 [JP] Japan .................................. 60-141677

[51] Int. Cl.$^5$ ............................................. C08J 9/16
[52] U.S. Cl. ....................................... 521/56; 521/60; 521/183; 521/189; 528/310; 528/328
[58] Field of Search ................... 521/183, 56, 60, 189; 528/310, 328

[56] References Cited

U.S. PATENT DOCUMENTS

| | | | |
|---|---|---|---|
| 2,572,844 | 10/1951 | MacDonald | 528/328 |
| 3,052,655 | 9/1962 | Fox et al. | 528/328 |
| 3,476,711 | 11/1969 | Muller et al. | 528/310 |
| 3,749,698 | 7/1973 | Lehmann et al. | 528/310 |
| 3,819,588 | 6/1974 | Fujimoto et al. | 528/328 |
| 4,334,056 | 6/1982 | Meyer et al. | 528/310 |

FOREIGN PATENT DOCUMENTS 53-39355 4/1978 Japan .
953237 3/1964 United Kingdom .

*Primary Examiner*—Morton Foelak
*Attorney, Agent, or Firm*—Fleit, Jacobson, Cohn, Price, Holman & Stern

[57] ABSTRACT

The present invention provides novel spherical grains of polyamino acid which can be used as a filler in chromatography, cosmetic powder and the like. The spherical grains can be produced by a method which comprises the steps of preparing a solution of hydrophobic polyamino acid such as poly n-leucine dissolved in an organic solvent; adding the solution to an aqueous medium and agitating said medium so as to obtain a dispersion of the spherical grains of the polyamino acid dispersed in the aqueous medium while evaporating the organic solvent; and taking out the spherical grains of polyamino acid from the dispersion.

5 Claims, 3 Drawing Sheets

SPHERICAL GRAINS OF POLYAMINO ACID AND PRODUCTION METHOD THEREOF

This is a divisional of application Ser. No. 117,925, filed Nov. 3, 1987, which is a continuation-in-part application of Ser. No. 878,683, filed June 26, 1986, now abandoned.

BACKGROUND OF THE INVENTION

1 Field of the Invention

The present invention relates to spherical grains used for various applications such as a filler in chromatography, a cosmetic powder and also to a method of producing such spherical grains.

2 Prior Art

Spherical grains of various materials conventionally find various uses such as fillers in various types of chromatography, cosmetic powders, and latices for investigation of biological reactions. Such spherical grains, however, still suffer problems and shortcomings which have to be solved. For example, a spherical particle gel of a dextran-based material, called Sephadex and frequently used as a filler for gel chromatography, has a limit in that the strength thereof needs to be increased by conducting a complicated crosslinking procedure because this filler has low strength under pressure. On the other hand, the region of the polymer which can be fractionated is reduced undesirably in molecular weight terms as the degree of crosslinking is increased.

SUMMARY OF THE INVENTION

The present inventors have found that various properties of spherical grains can be easily controlled by employing poly($\alpha$-amino acid), particularly synthetic poly ($\alpha$-amino acid) which is an entirely different raw material from those conventionally used for the applications described above.

Recently, investigations with respect to synthetic poly($\alpha$-amino acid) have progressed greatly and various applications of synthetic poly($\alpha$-amino acid) are now expected to be feasible. Moreover, there has been no example of the poly($\alpha$-amino acid) itself being spherically granulated. The inventors have established a method of producing spherical grains comprising synthetic poly($\alpha$-amino acid) as a matrix and this has led to the completion of this invention.

It is, therefore, a primary object of the present invention to provide novel spherical grains of poly($\alpha$-amino acid) which can be used for various applications.

Another object of the present invention is to provide a method for preparing such spherical grains.

These and other objects of the present invention will be clear from the following description.

In accordance with the present invention, there are provided novel spherical grains comprising poly($\alpha$-amino acid).

There is also provided a method of producing spherical grains which comprises the steps of adding a solution of hydrophobic poly($\alpha$-amino acid) dissolved in an organic solvent to an aqueous medium and agitating the medium while evaporating the organic solvent so as to obtain a dispersion of the spherical grains of poly($\alpha$-amino acid) dispersed in the aqueous medium; and taking out the spherical grains of poly($\alpha$-amino acid) from the dispersion.

DESCRIPTION OF THE PREFERRED EMBODIMENTS

Figure 1:
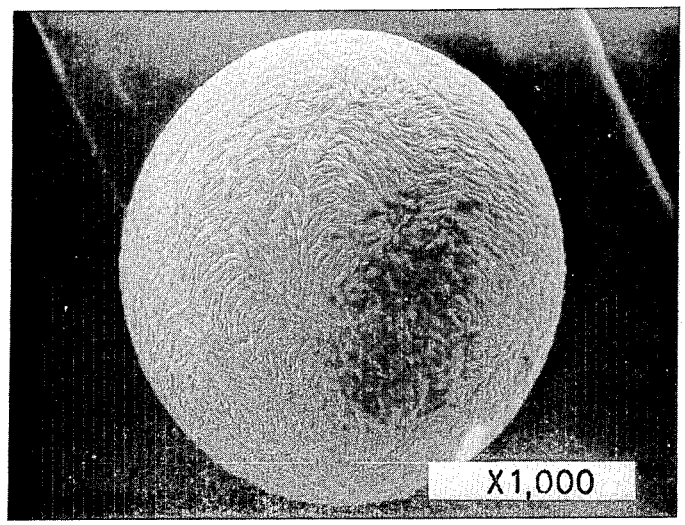
FIG. 1 is an electron microphotograph showing the surface structure of spherical grains obtained in Example 2 of the present invention.

As described above, there has been no conventional technique of spherically granulating poly($\alpha$-amino acid) itself. Hitherto, poly($\alpha$-amino acid) has been fixed to a suitable carrier (for example, polystyrene beads) so as to be provided for a separation operation of isomers. The present invention makes use of the fact that spherical grains of hydrophobic poly($\alpha$-amino acid) can be directly formed by adding a solution of a particular poly-($\alpha$-amino acid), that is hydrophobic poly($\alpha$-amino acid) dissolved in an organic solvent to an aqueous medium (in which the solution is insoluble or only slightly soluble) so as to suspend the poly($\alpha$-amino acid) therein. In the method of the present invention, liquid drops comprising the organic solvent containing hydrophobic poly($\alpha$-amino acid) are dispersed in the aqueous medium by adding the above-described solution to the aqueous medium and agitating it. As the agitation proceeds, the organic solvent is gradually evaporated so that a dispersion of the spherical grains of hydrophobic poly($\alpha$-amino acid) is obtained in the aqueous, medium. Then, the spherical grains of hydrophobic poly($\alpha$-amino acid) are taken out of the dispersion by a suitable separation technique (for example, filtration or centrifugation). The amino acids utilized in the present invention are $\alpha$-amino acids, which are defined by having the amino group and the carboxyl group in the amino acid bound to the same carbon atom. These poly($\alpha$-amino acid) can be easily prepared by a conventional method. A method of preparation of poly($\gamma$-methyl glutamate) is illustrated below by way of example:

(i) preparation of N-carboxy anhydride (hereinafter referred to as NCA)

$\gamma$-methyl glutamate is suspended in tetrahydrofuran, after which $COCl_2$ is charged into the solution at a temperature of 40° C. to obtain a transparent solution. After the excess $COCl_2$ has been distilled off, the solution is concentrated under reduced pressure, whereby NCA is obtained.

(ii) polymerization of NCA

The thus obtained NCA is dissolved in dichloroethane, and thereafter the NCA is polymerized by adding to the solution 2 to 0.5 equivalent of triethylamine (a polymerization catalyst) relative to NCA. As a result, poly ($\gamma$-methyl glutamate is obtained In this connection, NCA can easily be prepared by the Leuchs method, the Curtus method or preferably the above-described Fuchs-Fartling method.

In the present invention poly($\alpha$-amino acid) having any polymerization degree can be used. However, it is preferable to use a poly($\alpha$-amino acid) having a polymerization degree of 100 to 5000, more preferably 300 to 3000.

The hydrophobic poly(α-amino acid) used for obtaining a dispersion in an aqueous medium in accordance with the present invention includes naturally hydrophobic poly(α-amino acid) such as polyalanine, polyvaline, polyleucine, poly n-leucine, polythreonine, polymethionine, polycystine poly (phenylalanine), polytryptophane, poly(phenylglycine) and the like. Among these poly(α-amino acid), it is preferable to use polyalanine, polyvaline, polyleucine, polymethionine, polycystine, poly(phenylalanine), polytryptophane or poly(phenylglycine). There can be used those obtained by making hydrophilic poly(α-amino acids) hydrophobic (hydrophilic amino acid polymers having hydrophobic groups introduced). Such modified poly(α-amino acids) include hydrophobically esterified acid poly(α-amino acids) such as polygultamic acid and aspartic acid, for example, alkyl ester such as methyl, ethyl, propyl, t-butyl or octyl ester: aralkyl ester such as benzyl ester; cyclohexanemethyl ester; and tetrahydropyranmethyl ester of these amino acids. In this case, it is preferable to use methyl ester, ethyl ester, t-butyl ester, benzyl ester, cyclohexane methylester of polygultamic acid or polyaspartic acid. There can also be used hydrophobically carboxylated basic poly(α-amino acid) such as polylysine, polyarginine, polyhistidine, polyornithine, for example, carbobenzoxylated, carboethoxylated and carbo-t-butoxylated compounds of these amino acids. In this case, it is preferable to use carbobenzoxylated or carboethoxylated compounds of polylysine.

Furthermore, there can be used a poly(α-amino acid) in which a hydrophobic substrate such as benzyl group, t-butyl group or acetyl group is incorporated in a water-soluble neutral poly(α-amino acid) such as polyserine. In this case, it is preferable to use 0-benzyl polyserine or 0-tert-butyl polyserine. When these modified poly(α-amino acid) are used, spherical grains of the modified poly(α-amino acid) thus obtained may be used without any processing or may be changed into spherical grains of hydrophilic poly(α-amino acid) by removing the hydrophobic groups from the hydrophobic poly(α-amino acids), depending on the intended applications. That is to say, spherical grains of hydrophobic and hydrophilic poly(α-amino acid) (including amphiphatic, poly(α-amino acid) can be finally obtained in accordance with the present invention by employing hydrophobic poly(α-amino acid) during the preparation of the dispersion described above.

As described above, the method. of the invention employs a solution of hydrophobic poly(α-amino acid) dissolved in an organic solvent. The poly(α-amino acid) is dissolved in the organic solvent in an amount of 0.1 to 10 weight %, preferably 0.5 to 5 weight %. This organic solvent can form)liquid drops containing the hydrophobic poly(α-amino acid) when the solution is added to the aqueous medium and be evaporated by continuously agitating the aqueous medium. Therefore, the organic solvent used in the method of the invention should easily dissolve hydrophobic poly(α-amino acids), be insoluble in water, and have a lower boiling point than that of the aqueous medium. Preferred examples of this organic solvent are chloroform, dichloromethane, dichloroethane, and similar halogenated hydrocarbons, benzene, or a mixed solvent of these solvents.

For the purpose of preparing spherical grains of hydrophobic, poly(α-amino acids) in accordance with the present invention, a solution of hydrophobic poly(α-amino acids) dissolved in an organic solvent is added to an aqueous medium. Such a solution can be obtained by adding hydrophobic poly(α-amino acids) in such an organic solvent, as described above or more generally, it can be obtained as a polymerization solution of hydrophobic poly(α-amino acid) and can be used without any processing. Namely, a preferred embodiment of the present invention makes use of a solution obtained by polymerizing amino acids in an organic solvent to form hydrophobic poly(α-amino acid), without requiring any processing.

The grain size of the spherical grains of poly(α-amino acid) obtained can be easily controlled in accordance with the method of the present invention. The factors which control the grain size are mainly viscosity and the agitation speed of the organic solvent-aqueous medium system employed. In general, the grain diameter of the spherical grains obtained is increased as the poly-(α-amino acid) concentration in the organic solvent is increased and the viscosity of the aqueous medium system decreases. On the other hand, higher agitation speed causes the spherical grains size to be decreased. When regulating the grain diameter of the spherical grains by controlling the viscosity and the agitation speed of the organic solvent-aqueous medium system, it is preferred to add a viscosity modifier or to regulate the concentration of the polyamino acid solution. Suitable examples of the viscosity modifier are water-soluble polymers such as partially acetylated polyvinyl alcohol and gelatine. When fine grains for use as latices for biological reactions are to be obtained, it is preferable to add emulsifiers such as acetylpyridium salts and sorbic esters.

Furthermore, the invention makes it possible to produce porous spherical grains of opened cell structure, various porosity and pore sizes which can be employed at a filler in gel chromatography or a moisture- or air-permeable cosmetic powder. In order to obtain such porous spherical grains, an additive which is non-compatible with the poly(α-amino acid) compatible with organic solvent in which the poly(α-amino acid) is dissolved, insoluble in the aqueous medium, and has a higher boiling point than those of the organic solvent and the aqueous medium, is added to the solution of the hydrophobic poly(α-amino acid) dissolved in the organic solvent. As the solution is agitated in the presence of such an additive, liquid drops comprising the organic solvent are formed and the phase of this additive is separated in the poly(α-amino acid) solution. Thus, porous spherical grains of hydrophobic poly(α-amino acid) can be obtained by removing the additives in the latter processes and the degree of porosity and the pore diameter of the spherical grains can be controlled by adjusting the amount of the additive. The additive is contained in the organic solvent in an amount of 0.1 to 20 ml per g, preferably 0.5 to 10 ml per g of the hydrophobic poly(α-amino acid) dissolved in the organic solvent. As the additive used for obtaining the porous spherical grains, a crystalline substance such as naphthalene in a solid form may be added, and generally, liquids such as decalin, tetralin, toluene, xylene, ethylbenzene, diethylbenzene, anisole, hexanol, octanol, and dibutyl ether; aliphatic acids such as oleic acid, linolic acid and the like; and dialkyl phthalate such as dibutyl phthalate, dioctyl phthalate and the like and esters of aliphatic acids such as methyl dodecanate may be added.

According to the invention, it is thus possible to obtain spherical grains comprising poly($\alpha$-amino acid) as a matrix. Microscopic observation of the poly($\alpha$-amino acid) spherical grains of the present invention showed that the grains were spheres (particularly in the case of those having a large grain diameter) and the crystals of polypeptide were formed in aggregation. The poly($\alpha$-amino acid) spherical grains of the present invention are characterized by being rigid, as compared with conventionally used spherical grains such as Sephadex. The infrared absorption spectrum of the spherical grains of the present invention showed that a $\beta$-structure is at least partially present, the presence of such a $\beta$-structure being considered to further contribute to the hardening. The grain size of the spherical grains of the present invention can be controlled at will by producing them in accordance with the above-described method. Generally, the grain size of the spherical grains of the present invention is within the range of 0.1 to 500 $\mu$, preferably 1 to 300 $\mu$.

Furthermore, the pore diameter and the degree of porosity of the spherical grains of the present invention can be controlled at will over a wide range by producing them with use of the additive for making the grains porous, as described above. The pore diameter and the porosity vary in accordance with the desired application and the spherical grains obtained by the above-described method of the present invention can be controlled so as to have a pore diameter corresponding to $10^2$ (maltose) to $10^6$ (dextran) in terms of the molecular weight of water-soluble polysaccharide and a porosity of 10 to 95%. Thus, the spherical grains of the present invention can be controlled so as to maintain a suitable rigidity and possess a desired porosity without carrying out any hardening treatment such as crosslinking which is necessary with conventional spherical grains.

In accordance with the present, invention, spherical grains of hydrophobic poly($\alpha$-amino acid) can be obtained by using naturally hydrophobic poly($\alpha$-amino acid) and modified poly($\alpha$-amino acid) which, as the raw material, is made hydrophobic as described above. Such spherical grains of hydrophobic poly($\alpha$-amino acid) are particularly suitable for reversed phase chromatography and affinity chromatography. Spherical grains of a modified poly($\alpha$-amino acid) which is made hydrophobic but which has a relatively low, hydrophobic property, that is amphiphatic poly($\alpha$-amino acid) (for example, polymethyl or polyethyl glutamate), are preferably used as gel grains for utilization in gel chromatography both in water-systems and organic solvent-systems. In addition, the spherical grains of hydrophilic poly($\alpha$-amino acid) can be formed by removing the hydrophobic groups from the spherical grains obtained by using the modified poly($\alpha$-amino acid) which, as the raw material, is made hydrophobic by a conventionally known method, The spherical grains of hydrophilic poly($\alpha$-amino acid) can be used, for example, as ion-exchange spherical grains. The spherical grains of poly($\alpha$-amino acid) of the present invention can be used also as a cosmetic powder. Particularly, the porous spherical grains of amphiphatic poly($\alpha$-amino acid) described above are suitable for such applications.

The advantage of the present invention will be fully understood from the following description of the examples.

Example 1

5 g of polyleucine dissolved in 250 g of chloroform was dropped in 1000 ml of an aqueous solution containing 2 wt % of partially acetylated polyvinylalcohol and kept at 45° C. under agitation so as to suspend the polyleucine therein. As the solution was agitated for 24 hours, chloroform was evaporated, and polyleucine was aggregated to obtain poreless spherical grains. The spherical grains were collected by filtration and adequately washed with hot water and methanol to obtain polyleucine grains having a diameter of 44 to 75 $\mu$m at a yield of 80%

Example 2

5 g of poly-$\gamma$-benzyl-L-glutamate was dissolved in 200 ml of dichloromethane and suspended in an aqueous solution of 15 wt % partially acetylated polyvinylalcohol. After being agitated for 8 hours at 30° C., the suspension obtained was subjected to an after-treatment in accordance with the method used in Example 1 to obtain the intended poreless spherical grains having a diameter of 75 to 200 $\mu$m.

Figure 2:
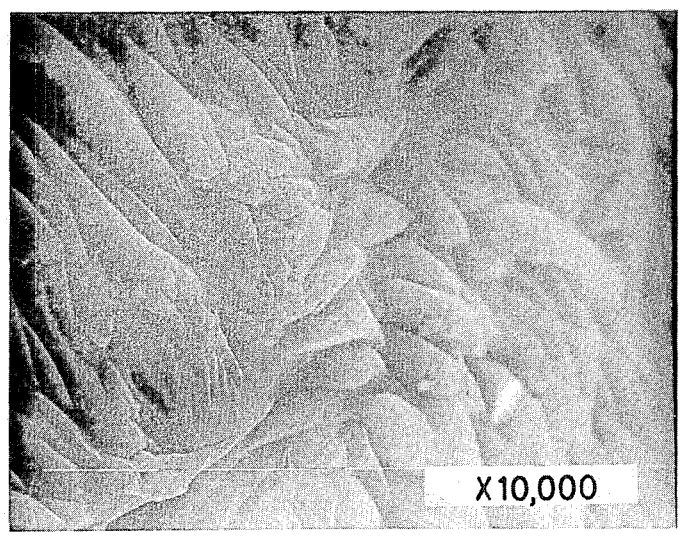
FIG. 2 is an enlarged electron microphotograph showing a part of surface structure of the spherical grains shown in FIG. 1.

Optical microscopic observation of the spherical grains obtained showed that the spherical grains of the present invention were substantially spheres and the crystals of polypeptide were formed in aggregation, as shown in FIGS. 1 and 2.

Example 3

3 g of partially dodecylated poly-$\alpha$-methylglutamate (a dodecylation rate of 35%) prepared by a conventional method was dissolved in 200 ml of a mixed solvent of dichloroethane/dichloromethane ($\frac{1}{4}$) and suspended in an aqueous solution containing 3.5 wt % of partially acetylated polyvinylalcohol. The suspension was agitated for 8 hours at 30° C. so as to evaporate the mixed solvent to obtain an aqueous dispersion of the spherical grains of partially dodecylated poly-$\gamma$-methylglutamate. The dispersion was concentrated by a centrifugal operation so as to separate tho spherical grains which were then sieved to obtain the poreless spherical grains of partially dodecylated poly-$\gamma$-methylglutamate having an average diameter of 5 to 15 $\mu$m (the porosity of 10% or less).

Example 4

Figure 3:
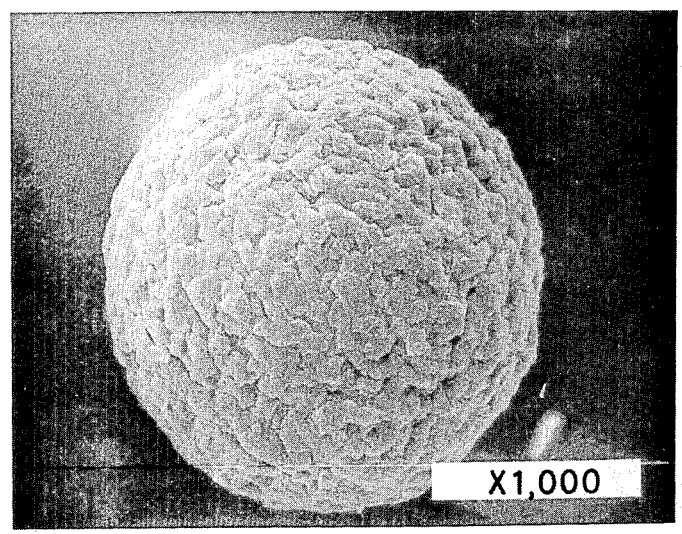
FIG. 3 is an electron microphotograph showing the surface structure of the spherical grains obtained in Example 4 of the present invention.
Figure 4:
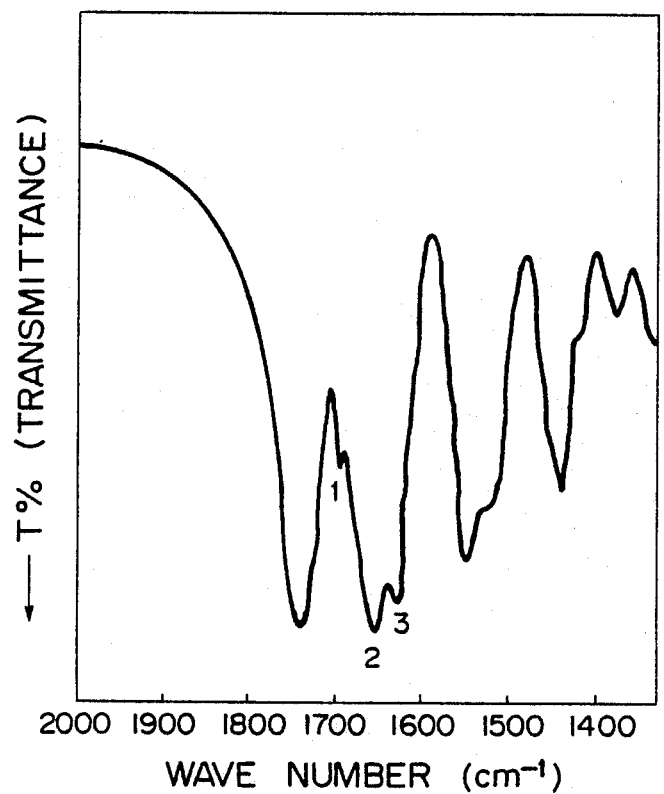
FIG. 4 is an infrared absorption spectrum of the spherical grains obtained in Example 4 of the present invention.

10 g of polymethyl glutamate and 10 ml of decalin (an additive for making grains porous) were dissolved in 400 ml of dichloroethane and the resulting solution was dropped in 2000 ml of an aqueous solution of 2 wt % partially acetylated polyvinylalcohol kept at 50° C. As the solution was vigorously agitated for 12 hours at the same temperature as the above, dichloroethane was evaporated to obtain the spherical grains of polymethyl glutamate containing decalin. These grains were washed by Soxhlet extraction method using acetone so as to remove decalin, then suspended in water, and fractionated into grain size groups by sieves meeting the JIS specification. The grain diameter of the main product was 25 to 44 $\mu$m, 90% or more of the grains obtained having a diameter of 10 to 105 $\mu$m. Optical microscopic observation of the grains obtained showed that they were spheres and had the porous structure as shown in FIG. 3. The infrared spectrum of the spherical grains, as shown in FIG. 4, showed the peaks of the carbonyl groups based on the reversed parallel $\beta$-structure (shown by 1 in the figure), the $\alpha$-helix structure (shown by 2 in the figure), and the parallel β-structure (shown by 3 in the figure). A conventional gel chromatography operation was carried out in an aqueous system for the purpose of estimating the porosity and the pore diameter of the spherical grains obtained. Namely, the spherical grains were charged in a column having an internal diameter of 5 mm and a length of 30 cm and homologues of dextran and maltose, polyhydric alcohols, and heavy water were eluted as standard samples, the relationship between the retention volumes and the molecular weights of the samples being extrapolated to a column void volume, and the molecular weight at this void volume was defined as an exclusion limit molecular weight (which could be considered as the maximum pore diameter). The porosity was calculated from the eluting position of heavy water. As a result, it was found that the spherical grains of poly (γ-methyl glutamate) had a maximum pore diameter corresponding to 8100 in terms of the molecular weight of dextran and the porosity of 70%.

Example 5

As an additive for making grains porous, 10 g of diethylbenzene or 30 g of n-octanol were dissolved in 400 ml of dichloroethane together with 10 g of polymethyl glutamate, and the spherical grains having the following characteristics were prepared by the same method as Example 4.

Spherical grain A (using diethylbenzene as the additive for making the grains porous)
  Grain diameter of main product: 25 to 44 μm
  Maximum pore diameter: 7000 in terms of the molecular weight of dextran
  Porosity 65%

Spherical grain B (using n-octanol as the additive for making the grains porous)
  Grain diameter of main product: 25 to 75 μm
  Maximum pore diameter: 10000 in terms of the molecular weight of dextran
  Porosity 65%

The spherical grains obtained were packed in a column having an internal diameter of 5 mm and a length of 30 cm and the separation of homologues and isomers of a lower alcohol was investigated using water as an eluate. The results obtained are shown as eluted volume ratios (k' values) in Table 1. As seen from the table, the spherical grains of poly(α-amino acid) of the present invention have excellent separation capability when used as gel grains for reversed phase chromatography. When acceptability for high speed as a filler for gel chromatography was investigated using the above-described column, the pressure loss was only 20 to 23 kg/cm$^2$ at a high flow rate of 5 ml/min. As a comparison, flow rate examination was carried out using Sephadex having the same maximum pore diameter as the above (G-50). This comparison showed the maximum flow rate which was as small as 2 ml/minute or so.

TABLE 1

| Sample species | Spherical grain A retention volume (ml) | k' | Spherical grain B retention volume (ml) | k' |
|---|---|---|---|---|
| Ethanol | 4.74 | 0.65 | 3.69 | 0.67 |
| iso-Propanol | 5.95 | 1.07 | 4.41 | 0.99 |
| iso-Butanol | 52 9.37 | 2.26 | 6.58 | 1.97 |
| tert-Butanol | 5.86 | 1.04 | 4.48 | 1.02 |
| sec-Butanol | 7.23 | 1.51 | 5.01 | 1.25 |

TABLE 1-continued

| Sample species | Spherical grain A retention volume (ml) | k' | Spherical grain B retention volume (ml) | k' |
|---|---|---|---|---|
| n-Butanol | 9.37 | 2.26 | 6.58 | 1.97 |

*The k' values were based on the retention volume of Blue Dextran.

Example 6

10 g of polyleucine and 20 g of diethylbenzene (an additive for making grains porous) were dissolved in 500 ml of chloroform, and the resulting solution was dropped in an aqueous solution of 2 wt % partially acetylated polyvinylalcohol kept at 45° C. so as to suspend the polyleucine therein. The suspension obtained was continuously agitated for 24 hours so as to evaporate chloroform to obtain a dispersion of spherical grains. Soxhlet extraction with methanol was repeated for 6 hours in order to remove diethylbenzene remaining in the grains. The spherical grains were collected by filtration and then washed with methanol and ether to obtain porous spherical grains of polyleucine having a diameter of 44 to 75 μ (the maximum pore diameter: $10^5$ in terms of the molecular weight of dextran, a porosity: 70%) at a yield of 75%.

Example 7

10 g of polymethyl glutamate and various additives for making grains porous shown in Table 2 were dissolved in 250 ml of dichloroethane and spherical grains were prepared by the same method as Example 4. The results of the measurements of the maximum pore diameters and the porosities of the grains are shown in Table 2. As seen from the table, the spherical grains of the present invention can be prepared so as to have the desired pore diameter and the porosity over a wide range and thus can be prepared so as to fractionate compounds having various molecular weights used as gel for gel chromatography.

TABLE 2

| Additive for making grains porous | Ratio to polyamino acid (wt %) | Exclusion molecular weight for dextran | Porosity (%) |
|---|---|---|---|
| Nothing | 0 | 60 | 10% or less |
| Butyl acetate | 100 | 100 | 19 |
| Toluene | 100 | 150 | 14 |
| o-Xylene | 100 | 150 | 17 |
| m-Xylene | 200 | 150 | 32 |
| p-Xylene | 100 | 150 | 20 |
| n-Hexanol | 100 | 1,000 | 16 |
| n-Octanol | 100 | 1,000 | 37 |
| n-Octanol | 300 | 10,000 | 65 |
| Diethylbenzene | 100 | 7,000 | 65 |
| Decalin | 100 | 8,000 | 70 |
| Decalin | 200 | 50,000 | 75 |
| methyl dodecanate | 200 | 2,000,000 | 90 |

Example 8

10 g of alkylester of polyglutamic acid containing dodecyl groups and methyl groups in a ratio of 32:68 as ester components was dissolved in a mixed solution of 10 ml of decalin and 400 ml of chloroform and the resulting solution was dropped in 2000 ml of an aqueous solution of 25 wt % partially acetylated polyvinylalcohol kept at 50° C. Chloroform was evaporated by vigorously agitating the suspension obtained at the same temperature for 24 hours. The spherical grains obtained were washed with ether so as to remove decalin and then filtrated to obtain porous spherical grains. The grain diameter of the main product was 10 μm to 25 μm, 90% or more of the product having a grain diameter of 1 to 44 μm.

The grains had the porosity of 68%.

In order to investigate the properties of the resulting grains as a cosmetic powder, oil absorption, water absorption, speed of oil absorption and speed of water absorption thereof were measured and compared with those of conventional cosmetic powders.

1 to 5 g of each sample was precisely weighed on a glass plate, and one droplet of oleic acid was dropped on the center of the sample through a buret at intervals of 3 to 7 seconds, together with sufficient kneading of the whole sample with a spatula. The above procedure was repeated until the end point, i.e., until the sample as a whole became such a hard putty-like mass that it formed into a spiral when worked with the spatula. Oil absorption was calculated from the following equation, using the oil amount added thereto up to the end point. However, in the case where the putty-like sample could not be formed into a spiral, the end point was determined as the time just before the sample suddenly softened and adhered to the glass plate upon addition of one droplet of oleic acid to the sample. The water absorption was measured by the same procedure as set forth above, except that distilled water was used instead of oleic acid.

$$A = W/S$$

wherein A represents oil absorption or water absorption [ml/g]; W represents amount of oil or distilled water added up to the end point [ml]; and S represents weight of the sample [g].

Speed of oil absorption was measured by pressing a predetermined amount of the sample into a cell and then dropping a predetermined amount of oleic acid on the surface of the pressed sample to observe the speed at which the oil was absorbed in the pressed sample. Speed of water absorption was measured by the same method as set forth above, except that distilled water was used.

The results obtained are shown in Table 3.

TABLE 3

| Sample | | Oil absorption | Water absorption | Speed of oil absorption | Speed of water absorption |
|---|---|---|---|---|---|
| Conventional powder | Fire silica Powder | 350 | 320 | ○ | ⊙ |
| | Kaolin | 50 | 60 | x | ⊙ |
| | Magnesium aluminum silicate | 300 | 310 | ○ | ⊙ |
| | Magnesium carbonate | 230 | 210 | ○ | ⊙ |
| Spherical grain of the present invention | | 180 | 90 | ⊙ | △ |

⊙ very rapid
○ rapid
△ relatively rapid
x very slow

As is obvious from Table 3, spherical grains of the present invention have suitably high amount of oil absorption and water absorption, high speed of oil absorption and slow speed of water absorption, compared with the conventional powders. As a result, the spherical powder of the present invention has suitable properties for use as a cosmetic powder.

What is claimed is:

1. A filler for use in chromatography which comprises porous spherical grains of poly (α-amino acid) having a porosity of 10 to 95%.

2. A filler according to claim 1, wherein the poly (α-amino acid) contains a β-structure.

3. A filler according to claim 1, wherein the spherical grains have a porous structure having a pore diameter of $10^2$ to $10^6$ in terms of the molecular weight of water-soluble polysaccharide.

4. A filler according to claim 1, wherein the diameter of the spherical grains is between 0.1 μ and 500 μ.

5. A filler according to claim 1, wherein the poly (α-amino acid) has a polymerization degree of 100 to 5000.

* * * * *